United States Patent
Berkcan et al.

(10) Patent No.: US 10,408,653 B2
(45) Date of Patent: *Sep. 10, 2019

(54) SYSTEM AND METHOD FOR METERING GAS BASED ON AMPLITUDE AND/OR TEMPORAL CHARACTERISTICS OF AN ELECTRICAL SIGNAL

(71) Applicant: Natural Gas Solutions North America, LLC, Houston, TX (US)

(72) Inventors: Ertugrul Berkcan, Clifton Park, NY (US); Nannan Chen, Clifton Park, NY (US); Roman Leon Artiuch, Houston, TX (US); Bo Li, Shanghai (CN)

(73) Assignee: Natural Gas Solutions North America, LLC, Houston, TX (US)

(*) Notice: Subject to any disclaimer, the term of this patent is extended or adjusted under 35 U.S.C. 154(b) by 68 days.

This patent is subject to a terminal disclaimer.

(21) Appl. No.: 15/362,582

(22) Filed: Nov. 28, 2016

(65) Prior Publication Data
US 2017/0074704 A1  Mar. 16, 2017

Related U.S. Application Data

(62) Division of application No. 14/561,431, filed on Dec. 5, 2014, now abandoned.

(51) Int. Cl.
*G01F 5/00* (2006.01)
*G01N 33/00* (2006.01)
(Continued)

(52) U.S. Cl.
CPC .............. *G01F 5/00* (2013.01); *G01F 1/3254* (2013.01); *G01F 7/00* (2013.01); *G01F 25/0053* (2013.01);
(Continued)

(58) Field of Classification Search
None
See application file for complete search history.

(56) References Cited

U.S. PATENT DOCUMENTS 4,429,571 A * 2/1984 Kullmann .............. G01F 7/00
73/197
4,546,649 A  10/1985 Kantor
(Continued)

FOREIGN PATENT DOCUMENTS

EP  2312276 A1  4/2011
JP  2003075214 A  3/2003
(Continued)

OTHER PUBLICATIONS

Nguyen et al., "Speed control of PIG using bypass flow in natural gas pipeline", Industrial Electronics, 2001. Proceedings. ISIE 2001. IEEE International Symposium on (vol. 2) 2001, pp. 863-868.
(Continued)

*Primary Examiner* — Harshad R Patel
(74) *Attorney, Agent, or Firm* — Paul Frank + Collins P.C.

(57) ABSTRACT

A system for metering gas includes a housing configured to allow a flow of the gas between an input port and an output port. Further, the system includes a flow manager disposed in the housing and configured to modify at least one physical characteristic of the flow of the gas in the housing. Furthermore, the system includes a flow sensor disposed in the housing and configured to generate an electrical signal in response to flow characteristics of the gas in the housing. Moreover, the system also includes a processor configured to determine at least one flow parameter of the gas based on an amplitude characteristic of the electrical signal, a temporal characteristic of the electrical signal, or both the amplitude characteristic and the temporal characteristic of
(Continued)

the electrical signal. A method for metering the gas is also presented.

12 Claims, 5 Drawing Sheets

(51) Int. Cl.
*G01F 7/00* (2006.01)
*G01F 1/32* (2006.01)
*G01F 25/00* (2006.01)

(52) U.S. Cl.
CPC ..... *G01N 33/0006* (2013.01); *G01N 33/0062* (2013.01)

(56) References Cited

U.S. PATENT DOCUMENTS

| | | | |
|---|---|---|---|
| 5,029,470 A | 7/1991 | Gamperl | |
| 5,080,131 A | 1/1992 | Ono et al. | |
| 5,117,856 A * | 6/1992 | Kim | G01F 7/00 137/110 |
| 5,159,951 A | 11/1992 | Ono et al. | |
| 5,249,462 A * | 10/1993 | Bonne | G01F 1/6842 428/116 |
| 5,339,695 A * | 8/1994 | Kang | G01F 1/3227 73/195 |
| 5,463,899 A * | 11/1995 | Zemel | G01F 1/68 73/195 |
| 5,861,561 A | 1/1999 | Van Cleve et al. | |
| 5,864,067 A * | 1/1999 | Ligneul | F15C 1/22 73/861.21 |
| 5,869,758 A * | 2/1999 | Huiberts | G01F 1/6842 73/197 |
| 6,655,207 B1 * | 12/2003 | Speldrich | G01F 1/40 73/202.5 |
| 6,684,692 B1 * | 2/2004 | Lenzing | G01F 1/6842 73/202.5 |
| 7,212,953 B1 | 5/2007 | Artiuch | |
| 7,866,208 B1 | 1/2011 | Ueda et al. | |
| 8,342,018 B2 | 1/2013 | Huang et al. | |
| 8,418,549 B2 | 4/2013 | Speldrich et al. | |
| 8,499,786 B2 * | 8/2013 | Zolock | G05D 7/0635 137/487 |
| 8,826,731 B2 * | 9/2014 | Speldrich | F17D 1/00 73/204.21 |
| 10,139,259 B2 * | 11/2018 | Chen | E21B 43/34 |
| 2001/0052263 A1 * | 12/2001 | Setescak | F02D 41/187 73/204.21 |
| 2007/0084286 A1 | 4/2007 | Ajay et al. | |
| 2007/0099527 A1 | 5/2007 | Brun et al. | |
| 2007/0112536 A1 | 5/2007 | Artiuch et al. | |
| 2008/0066527 A1 | 3/2008 | Ajay | |
| 2009/0187356 A1 | 7/2009 | Articuh | |
| 2010/0139389 A1 * | 6/2010 | Morita | G01F 1/6845 73/204.11 |
| 2011/0061469 A1 | 3/2011 | Maahs | |
| 2011/0166800 A1 | 7/2011 | Berkcan et al. | |
| 2011/0226052 A1 * | 9/2011 | Speldrich | B01D 17/10 73/204.22 |
| 2011/0226053 A1 * | 9/2011 | Sorenson | B01D 17/10 73/204.23 |
| 2011/0247390 A1 * | 10/2011 | Smirnov | G01F 25/0053 73/1.16 |
| 2011/0303019 A1 | 12/2011 | Gysling | |
| 2012/0125337 A1 | 5/2012 | Asanoi | |
| 2012/0174650 A1 | 7/2012 | Ariessohn et al. | |
| 2013/0079667 A1 | 3/2013 | Berkcan et al. | |
| 2014/0165718 A1 | 6/2014 | Berkcan et al. | |
| 2014/0260667 A1 | 9/2014 | Berkcan et al. | |

FOREIGN PATENT DOCUMENTS

| | | |
|---|---|---|
| JP | 2003149016 A | 5/2003 |
| WO | 199502812 A1 | 1/1995 |
| WO | 2014151003 A2 | 9/2014 |

OTHER PUBLICATIONS

Albusaidi et al., "Measurement of multiple velocities in multiphase flow", Advances in Sensors for Fluid Flow Measurement, IEEE Colloquium on, Apr. 18, 1996, pp. 12/1-12/4.

European Search Report and Written Opinion issued in connection with corresponding EP Application No. 15196759.6-1553 dated Jun. 24, 2016.

International Search Report and Written Opinion, dated Apr. 24, 2019, in related PCT/US2018/068081.

* cited by examiner

SYSTEM AND METHOD FOR METERING GAS BASED ON AMPLITUDE AND/OR TEMPORAL CHARACTERISTICS OF AN ELECTRICAL SIGNAL

CROSS-REFERENCE TO RELATED APPLICATIONS

This application is a divisional and claims priority to U.S. Non-provisional patent application Ser. No. 14/561,431, filed on Dec. 5, 2014, entitled "SYSTEM AND METHOD FOR METERING GAS BASED ON AMPLITUDE AND/OR TEMPORAL CHARACTERISTICS OF AN ELECTRICAL SIGNAL," (originally titled "SYSTEM AND METHOD FOR METERING GAS"), which is incorporated by reference in its entirety and is assigned to the assignee of the present invention.

BACKGROUND

Embodiments of the present disclosure relate to measurement of a flow of fluids, and more particularly to a system and method for metering gas.

Currently, metering of gas entails use of various types of flow sensing devices such as mass flow sensing devices to measure a mass flow rate of fluids. Some flow sensors determine the mass flow rate of the gas based on an amplitude measurement. Other flow sensing devices involve vortex-based sensing where, for example, a frequency at which vortices are formed is essentially proportional to the flow rate of the fluid. Consequently, the volumetric flow rate is determined based on the frequency at which the vortices are formed.

Generally, the currently available gas metering systems offer the advantage of high sensitivity in a low flow range. However such gas metering systems are typically adversely impacted by gas density fluctuations, moisture fluctuations, gas mixture fluctuations, and the like. Consequently, such gas metering systems fail to provide a direct and accurate volumetric flow rate measurement. For example, the density of the gas may vary depending on factors such as pressure, temperature, and composition of the gas. These factors adversely affect the quality and accuracy of flow measurement. On the contrary, the vortex-based sensing devices entail direct volumetric flow rate measurement. However, measurement of the flow rate using the vortex-based sensing devices is adversely impacted when a velocity of the gas is low as the low velocity of the gas affects formation of vortices.

BRIEF DESCRIPTION

In accordance with aspects of the present specification, a system for metering gas is disclosed. The system includes a housing having an input port and an output port, where the housing is configured to allow a flow of the gas between the input port and the output port. Further, the system includes a flow manager disposed in the housing. The flow manager is configured to modify at least one physical characteristic of the flow of the gas in the housing. Furthermore, the system includes a flow sensor disposed in the housing. The flow sensor is configured to generate an electrical signal in response to flow characteristics of the gas in the housing. Moreover, the system also includes a processor operatively coupled to the flow manager and the flow sensor. The processor is configured to determine at least one flow parameter of the gas based on an amplitude characteristic of the electrical signal, a temporal characteristic of the electrical signal, or both the amplitude characteristic and the temporal characteristic of the electrical signal.

In accordance with another aspect of the present specification, a method for metering gas is disclosed. The method includes modifying at least one physical characteristic of a flow of the gas in a housing. Moreover, the method also includes generating an electrical signal in response to a flow characteristic of the gas in the housing. Further, the method includes determining at least one flow parameter of the gas based on an amplitude characteristic of the electrical signal, a temporal characteristic of the electrical signal, or both the amplitude characteristic and the temporal characteristic of the electrical signal.

DRAWINGS

These and other features, aspects, and advantages of the present specification will become better understood when the following detailed description is read with reference to the accompanying drawings in which like characters represent like parts throughout the drawings, wherein.

DETAILED DESCRIPTION

The specification may be best understood with reference to the detailed figures and description set forth herein. Various embodiments are described hereinafter with reference to the figures. However, those skilled in the art will readily appreciate that the detailed description given herein with respect to these figures is for explanatory purposes as the method and the system extend beyond the described embodiments.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

Figure 1:
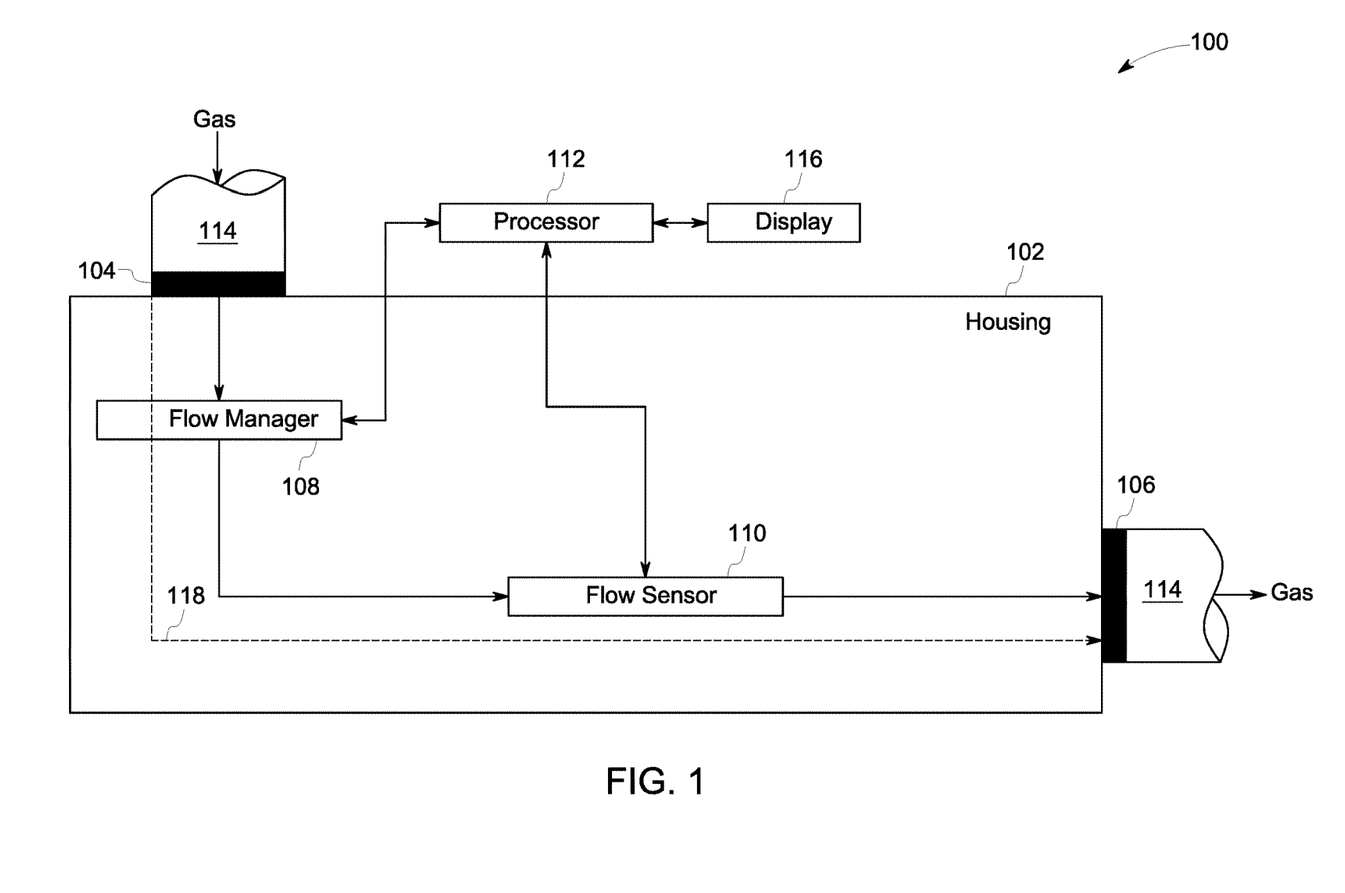
FIG. 1 is a diagrammatical illustration of a system for metering gas, in accordance with aspects of the present specification.

FIG. 1 is a diagrammatical illustration of a system 100 for metering gas, in accordance with aspects of the present specification. The system 100 includes a housing 102 having an input port 104 and an output port 106. In addition, the system 100 includes a flow manager 108, a flow sensor 110, and a processor 112. Optionally, the system 100 may also include a display 116. The flow manager 108 and the flow sensor 110 may be disposed within the housing 102. The processor 112 may be disposed on a printed circuit board (PCB) (not shown). In one embodiment, the PCB may be disposed on or about the housing 102. Moreover, the system 100 may also include an energy source such as a battery (not shown) coupled to the flow manager 108, the flow sensor 110, and the processor 112. The energy source may supply energy to the flow manager 108, the flow sensor 110, and the processor 112. In one embodiment, the flow manager 108 may be disposed in the proximity of the input port 104. In another embodiment, the flow manager 108 may be disposed in the proximity of the output port 106.

The system 100 may be operatively coupled to a pipeline 114 as shown in FIG. 1 and configured to meter a gas flowing through the pipeline 114. More particularly, the system 100 may be operatively coupled to the pipeline 114 such that the gas flowing through the pipeline 114 is received at the input port 104. Moreover, the housing 102 and the output port 106 may be arranged such that the gas is discharged from the output port 106. In one embodiment, a flow path of at least a portion of the gas flowing in the housing 102 may be indicated by a dashed line 118. The pipeline 114 may be a part of a household or an industrial setup for supplying gas, such as a natural gas. In one embodiment, the input port 104 and the output port 106 may form an integral part of a body of the housing 102. In some other embodiments, the input port 104 and the output port 106 may be operatively coupled to the housing 102. As noted hereinabove, the system 100 may be configured to meter the gas flowing through the pipeline 114. The term 'meter' as used herein may be used to refer to determining one or more flow parameters of the gas including, but not limited to, a mass flow rate, an accumulated volume of the gas, a volumetric flow rate, a cumulative gas volume per a determined time unit, or combinations thereof.

The housing 102 may be configured to receive the gas from the input port 104. In addition, the housing 102 may further be configured to allow a flow of the gas from the input port 104 to the output port 106. As previously noted, the flow manager 108 and/or the flow sensor 110 may be disposed within the housing 102. More particularly, in one embodiment, the flow manager 108 and/or the flow sensor 110 may be arranged in the housing 102 such that the flow manager 108 and/or the flow sensor 110 are in the flow path 118 of at least a portion of the gas flowing from the input port 104 to the output port 106.

As will be appreciated, various physical characteristics associated with the flow of the gas flowing in the system 100 including, but not limited to, a separability of the flow of the gas, a pressure of the gas, a temperature of the gas, and a level of impurities in the gas affect the measurement results. Accordingly, it may be desirable to account for one or more of these physical characteristics while metering the gas. In accordance with the aspects of the present specification, the flow manager 108 is configured to modify at least one physical characteristic of the flow of the gas in the housing 102 in order to minimize the effect of the one or more of the physical characteristics on the measurement determined by the system 100.

The term "separability of the flow of the gas" as used herein may be used to refer to an ability to cause a separation of the flow of the gas in a vicinity of a surface such as a surface of the housing 102 where the effect of viscosity of the gas may be significant. Typically, in fluid mechanics, a boundary layer is a layer of fluid (e.g., the gas) in the vicinity of a bounding surface such as the surface of the housing 102 where the effect of the viscosity of the gas may be significant. As will be appreciated, the separation of the flow of the gas occurs when the boundary layer travels far enough against a pressure gradient that a speed of the boundary layer relative to the object (e.g., the surface of the housing 102) becomes substantially close to zero. Consequently, the separation of the gas flow may lead to formation of eddies and vortices. By way of example, the separability of the flow of the gas may be related to the lack of laminarity of the flow of the gas. More particularly, the separability of the flow of the gas may result in the separation of the boundary layer such as a laminar boundary layer.

In one embodiment, at least a portion of the gas flows by the flow manager 108. Moreover, a portion of the gas in the housing 102 may also flow through the flow sensor 110. The flow sensor 110 may be configured to generate an electrical signal such as a voltage signal or a current signal in response to the flow characteristics of the gas in the housing 102. The term 'electrical signal' is hereinafter also referred to as a signal. Some examples of the flow sensor 110 include, but are not limited to, a calorimetric flow sensor, a hot wire anemometer, a mass flow rate sensor, a volumetric flow rate sensor, a pressure sensor, a temperature sensor, or combinations thereof. Moreover, the flow sensor 110 may also include one or more sensing elements (not shown in FIG. 1). Examples of the sensing elements may include, but are not limited to, micro-electromechanical flow sensing elements, thermopiles, temperature sensing elements, pressure sensing elements, or combinations thereof. The electrical signal generated by the flow sensor 110 may have an amplitude characteristic and a temporal characteristic. The amplitude characteristic may include, but is not limited to, a magnitude, a scale, a breadth, or combinations thereof. Similarly, the temporal characteristic may include, but is not limited to, a period, a frequency, a zero crossing rate, a phase, a time-resolved demodulation, a frequency-resolved demodulation of the signal, or combinations thereof.

Furthermore, the processor 112 is operatively coupled to the flow manager 108 and the flow sensor 110. In one embodiment, the processor 112 may be configured to control the functionality of the flow manager 108 to aid in the modification of the physical characteristics of the flow of the gas in the housing 102. More particularly, the processor 112 may be configured to control the flow manager 108 to allow the flow manager 108 to modify one or more physical characteristics of the gas in the housing 102. It may be noted that it may be desirable to maintain the values of the one or more physical characteristics within corresponding desirable ranges of values. In one embodiment, the desired ranges of values of the one or more physical characteristics may be stored in memory (not shown) associated with the processor 112.

In another embodiment, the processor 112 may be configured to receive the electrical signal generated by the flow sensor 110. Furthermore, the processor 112 may also be configured to determine at least one flow parameter of the gas based on the electrical signal received from the flow sensor 110. Some examples of the flow parameter include, but are not limited to, the mass flow rate of the gas, the accumulated volume of the gas, the volumetric flow rate of the gas, the cumulative gas volume per the determined time unit, or combinations thereof. More particularly, the processor 112 is configured to determine the flow parameter based on the amplitude characteristic, the temporal characteristic, or both the amplitude characteristic and the temporal characteristic of the electrical signal.

In one example, the processor 112 may be a signal processor. In this embodiment, the processor 112 may be configured to perform a spectral analysis of the electrical signal received from the flow sensor 110. Some examples of signal processing techniques that may be implemented by the processor 112 to perform the spectral analysis may include, but are not limited to, a Fast Fourier Transform (FFT), the heterodyne principle, a phase-locked loop, or combinations thereof.

Additionally, in certain embodiments, the system 100 may include the display 116. In one embodiment, the values of the flow parameter determined by the processor 112 may be visualized on the display 116. By way of example, the display 116 may include a light emitting diode (LED) display, a liquid crystal display (LCD), and the like. In one embodiment, the display 116 may be disposed on the housing 102. However, in certain embodiments, the display 116 may be disposed at a remote location. The display 116 may be communicatively coupled to the processor 112. In one embodiment, the display 116 may be coupled to the processor 112 via a wired medium. In such an instance, serial or parallel communication protocols may be implemented to aid in the data communication between the processor 112 and the display 116.

In another embodiment, the display 116 may be coupled to the processor 112 via a wireless communication link. In such a configuration, the system 100 may further include a wireless communication unit (not shown) to aid in the data communication between the processor 112 and the display 116 over the wireless communication link. By way of example, the wireless communication unit may use wireless communication protocols such as Bluetooth or Wi-Fi. In certain embodiments when the display 116 is disposed at the remote location, the wireless communication unit may use wireless communication protocols such as Wi-Max and/or cellular communication protocols such as 2G, 3G, or 4G.

In yet another embodiment, an additional display may be provided at the remote location in addition to the display 116 disposed on the housing 102. The additional display may be coupled to the processor 112 via a wireless communication link. The wireless communication unit may aid in the data communication between the processor 112 and the remotely disposed display over the wireless communication link.

Implementing the system 100 for metering gas a described with respect to FIG. 1 aids in determining flow parameters such as the mass flow rate of the gas, the accumulated volume of the gas, the volumetric flow rate of the gas, the cumulative gas volume per the determined time unit, or combinations thereof. Moreover, the flow parameters thus determined may not be impacted by gas density fluctuations, moisture fluctuations, gas mixture fluctuations, and the like.

Figure 2:
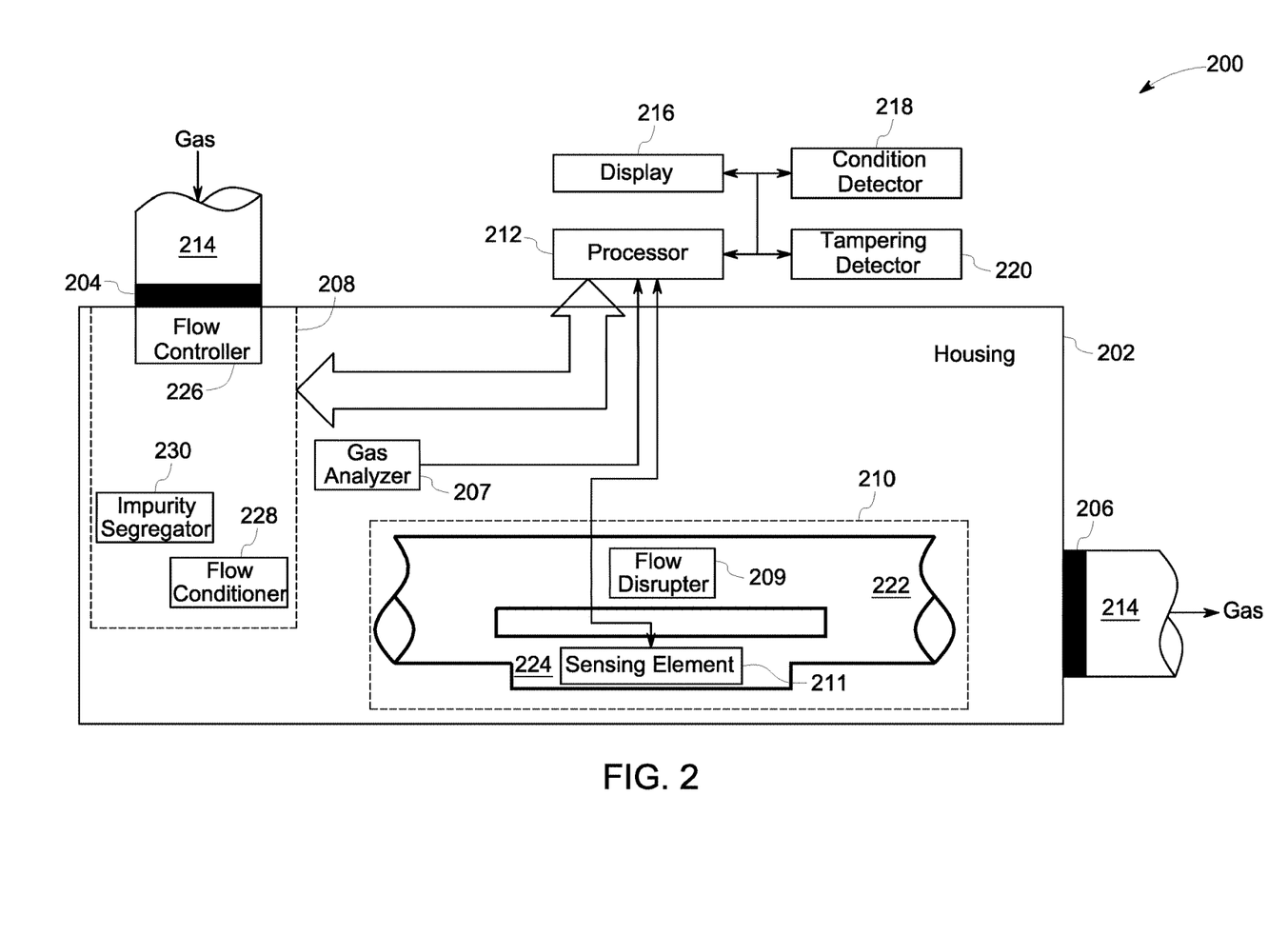
FIG. 2 is a diagrammatical illustration of another system for metering gas, in accordance with aspects of the present specification.

FIG. 2 is a diagrammatical illustration of another embodiment of system 200 for metering gas, in accordance with aspects of the present specification. FIG. 2 is discussed in conjunction with the elements of FIG. 1. The system 200 includes a housing 202 having an input port 204 and an output port 206. In a presently contemplated configuration, the system 200 may further include a flow manager 208, a gas analyzer 207, a flow sensor 210, a processor 212, a condition detector 218, and a tampering detector 220. The system 200 may also include a display 216. Moreover, the system 200 may also include an energy source such as a battery (not shown) and a wireless communication unit (not shown). The energy source may supply energy to the flow manager 208, the gas analyzer 207, the flow sensor 210, the processor 212, the condition detector 218, and the tampering detector 220. The wireless communication unit may be coupled to the processor 212. It may be noted that the arrangement and/or the functionality of the housing 202, the input port 204, the output port 206, the flow manager 208, the flow sensor 210, the processor 212, a pipeline 214, the display 216, the energy source, and the wireless communication unit may be similar to the corresponding elements of FIG. 1.

In one embodiment, the system 200 may be operatively coupled to the pipeline 214 and configured for metering the gas flowing through the pipeline 214. By way of example, in the embodiment of FIG. 2, the system 200 is configured to determine a flow parameter such as a volumetric flow rate of the gas flowing through the pipeline 214. The system 200 may also be configured to determine other flow parameters including, but not limited to, a mass flow rate of the gas, an accumulated volume of the gas, a cumulative gas volume per a determined time unit, or combinations thereof.

In one embodiment, the flow manager 208 may be arranged in the housing 202. The flow manager 208 is configured to modify the at least one physical characteristic of the flow of the gas in the housing 202. In one example embodiment, the flow manager 208 may include a flow controller 226, a flow conditioner 228, and an impurity segregator 230.

The flow controller 226 may include a shut-off valve (not shown) configured to selectively stop the flow of the gas from the input port 204 to the output port 206, or vice-versa. In one embodiment, the shut-off valve may be disposed in the proximity of the input port 204. In another embodiment, the shut-off valve may be disposed in the proximity of the output port 206. Moreover, the flow conditioner 228 may be configured to control a separability of the flow of the gas in the housing 202. The control of the separability of the flow of the gas may include reducing turbulences, swirls, and/or asymmetric flow profiles in the flow of the gas.

The impurity segregator 230 may be configured to remove impurities from the gas flowing through the housing 202. The impurities in the gas, such as natural gas, may include, but are not limited to, one or more of dust, foreign objects, glycol, hydrogen sulfide ($H_2S$), sulfur dioxide ($SO_2$), methyl mercaptan ($CH_4S$), carbonyl sulfide (OCS), carbon disulfide ($CS_2$), nitrogen, carbon dioxide ($CO_2$), water vapor, and combinations thereof. Various examples of the impurity segregator 230 may include, but are not limited to, a cyclone type dust segregator, charcoal, activated carbon, monoethlamine (MEA) solution, a bed of iron filings, and the like. In one embodiment, the impurity segregator 230 may be disposed proximate to an internal surface of the housing 102. More particularly, the impurity segregator 230 may be disposed proximate to any corner of the housing 202. In such a configuration, the impurities removed by the impurity segregator 230 may be deposited about the corner of the housing 202. However, in certain embodiments, the impurity segregator 230 may be positioned at other locations within the housing 202.

Further, in certain embodiments, the gas analyzer 207 may also be disposed in the housing 202. In one embodiment, the gas analyzer 207 may be disposed such that the gas analyzer 207 is aligned with one or more elements of the flow manager 208. In other embodiments, the gas analyzer 207 may be disposed at other locations within the housing 202. The gas analyzer 207 is configured to determine one or more non-flow rate characteristics of the gas. In one example, the non-flow rate characteristics of the gas may include characteristics such as, but not limited to, a gas density, a gas mixture and composition, a gas temperature, a gas pressure, humidity, an energy content of the gas, levels of various impurities contained in the gas, or combinations thereof. Furthermore, the gas analyzer 207 may include one or more sensors that aid in the determination of constituents of the gas, temperature, pressure, and caloric value (indicative of the energy content) of the gas, and/or levels of various impurities in the gas flowing through the housing 202. The gas analyzer 207 may also be configured to communicate the determined values of the non-flow rate characteristics to the processor 212.

Moreover, the flow sensor 210 is also disposed in the housing 202. Some examples of the flow sensor 210 include, but are not limited to, a calorimetric flow sensor, a hot wire anemometer, a mass flow rate sensor, a volumetric flow rate sensor, a pressure sensor, a temperature sensor, or combinations thereof. For the purpose of simplicity of illustration, in one example of FIG. 2, the flow sensor 210 is described as being combination of the mass flow rate sensor and the volumetric flow rate sensor. In one embodiment of the present specification, the flow sensor 210 may include one or more of a flow conduit 222, a bypass channel 224, a flow disrupter 209, and one or more sensing elements such as a sensing element 211. The flow conduit 222 may be configured to allow therethrough, at least a portion of the flow of the gas flowing in the housing 202.

Moreover, in one embodiment, the flow disrupter 209 may be disposed in the flow conduit 222, as depicted in FIG. 2. Although in the embodiment of FIG. 2, the flow disrupter 209 is shown to be a part of the flow sensor 210, use of the flow disrupter 209 with the flow manager 208 and/or the gas analyzer 207 is also contemplated. In an instance when the flow disrupter 209 is disposed within the gas analyzer 207, the flow disrupter may aid in the determination of the non-flow rate characteristics of the gas. In certain embodiments, the flow disrupter 209 may be disposed outside the flow sensor 210 in the housing 202.

The flow disrupter 209 may be configured to impart disturbances to the flow of the gas in the housing 202 and/or the flow conduit 222. The disturbances produced in the flow of the gas may be in the form of vortices, pressure, and/or velocity fluctuations. The flow disrupter 209 may have shapes including, but not limited to, a blunt flow disrupter, a planar flow disrupter, a rectangular flow disrupter, and combinations thereof.

The bypass channel 224 may be in fluid communication with the flow conduit 222. More particularly, as depicted in FIG. 2, in one embodiment, the bypass channel 224 may be positioned such that the bypass channel 224 is disposed external to the flow conduit 222. In other embodiments, the bypass channel 224 may be disposed within the flow conduit 222.

In one example embodiment, the flow conduit 222, the bypass channel 224, the flow disrupter 209, and/or the sensing element 211 may be configured to have a geometrical relationship. Some example parameters that may be used to determine the geometrical relationship between the bypass channel 224, the flow conduit 222, the flow disrupter 209, and the sensing element 211 may include, but are not limited to, respective dimensions of the bypass channel 224, the flow conduit 222, and the flow disrupter 209, positioning of the flow disrupter 209 in the flow conduit 222 relative to the bypass channel 224 and/or the sensing element 211, the dimensions of the flow disrupter 209 with respect to the dimensions of the flow conduit 222, or combinations thereof. Furthermore, the geometrical relationship between the flow conduit 222, the bypass channel 224, the flow disrupter 209, and/or the sensing element 211 may be selected such that the geometrical relationship aids in establishing a phase difference between a pressure of the gas flow at the input of the bypass channel 224 and a pressure of the gas flow at the output of the bypass channel 224. Furthermore, a value of this phase difference may be selected such that the phase difference results in an increase in a signal-to-noise ratio of an electrical signal generated by the sensing element 211. By way of example, the phase difference may be selected such that the flow pressure at the input of the bypass channel 224 and the flow pressure at the output of the bypass channel 224 are substantially out-of-phase relative to one another. Such a phase difference may aid in effectively suppressing common mode noise effects in the electrical signal generated by the sensing element 211.

In one embodiment, the bypass channel 224 and the flow disrupter 209 are arranged in the flow conduit 222 such that at least some flow characteristics of the gas flowing in the bypass channel 224 are affected. By way of example, the bypass channel 224 and the flow disrupter 209 may be positioned such that the flow rate of the gas flowing in the bypass channel 224 is altered. More particularly, in one embodiment, the flow conduit 222, the bypass channel 224, and the flow disrupter 209 may be dimensioned and arranged such that when the flow rate of the gas flowing through the flow conduit 222 is low (laminar flow) no disturbance is imparted to the flow of the gas in the flow conduit 222. Consequently, no vortices are formed in the flow conduit 222 when the flow of the gas is laminar. A range of such low flow rates for which the vortices are not formed in the flow conduit 222 may generally be referred to as a first flow regime.

In another embodiment, the flow conduit 222, the bypass channel 224, and the flow disrupter 209 may be dimensioned and arranged such that when the flow rate of the gas flowing through the flow conduit 222 is high, disturbances may be imparted to the flow of the gas by the flow disrupter 209. Consequently, vortices are formed in the gas flowing in the flow conduit 222 when the flow rate of the gas is high. The term "second flow regime" may be used to refer to a range of such high flow rates that result in the formation of the vortices in the gas flowing in the flow conduit 222. In the second flow regime, the vortices may be formed such that the temporal characteristic, for example, the frequency ($V_f$) of the vortices is proportional to the volumetric flow rate of the gas flowing through the flow conduit 222.

Furthermore, in one embodiment, the sensing element 211 may be disposed in the bypass channel 224. In another embodiment, the sensing element 211 may be disposed in the flow conduit 222. Examples of the sensing element 211 may include, but are not limited to, micro-electromechanical flow sensing element, a thermopile, a temperature sensing element, a pressure sensing element. In one embodiment, the thermopile, temperature sensing element, and pressure sensing element may include one or more micro-electromechanical sensing (MEMS) elements. The disturbances imparted by the flow disrupter 209 in the second flow regime may cause oscillatory pressure fluctuations at the input and/or output of the bypass channel 224. Such oscillatory pressure fluctuations may in turn cause a measurable frequency modulation of the flow of the gas flowing through the bypass channel 224. It may be noted that flow rates corresponding to the first flow regime may result in a substantially steady pressure at the input and output of the bypass channel 224 or a steady flow in the bypass channel 224.

As previously noted, the sensing element 211 of the flow sensor 210 is configured to generate the electrical signal in response to the flow characteristics of the gas flowing in the housing 202. For example, the electrical signal may be a voltage (V) signal or a current (I) signal. Accordingly, in the second flow regime where the vortices are formed in the gas flowing through the flow conduit 222, the sensing element 211 may generate an alternating current (AC) voltage signal. The frequency ($V_f$) of the AC voltage signal thus generated is proportional to or directly related to a volumetric flow rate (e.g., liter/second) of the gas flowing through the housing 202. For ease of explanation, a parameter such as the frequency ($V_f$) is used to represent temporal characteristics of the AC voltage signal. However, embodiments of the present specification are also applicable to other temporal characteristics of the AC voltage signal. In one embodiment, the generated AC voltage signal may be at an offset from a zero value. Accordingly, the AC voltage signal thus generated may also have a direct current (DC) value.

However, in the first flow regime where no vortices are formed, the sensing element 211 of the flow sensor 210 may generate a DC voltage having a magnitude ($V_{amp}$) which is related to a mass flow rate (e.g., kilogram/second) of the gas flowing through the housing 202. As will be appreciated, the volumetric flow rate of the gas may be determined based at least on the density of the gas. Also, as noted previously, the density of the gas may vary substantially depending on various factors associated with the gas, such as the pressure, temperature, gas composition, or combinations thereof. Hence, in the first flow regime, the mass flow rate of the gas may not be a clear indicator of the volumetric flow rate of the gas. Consequently, determining the volumetric flow rate based on the mass flow rate may be laborious task.

Figure 3:
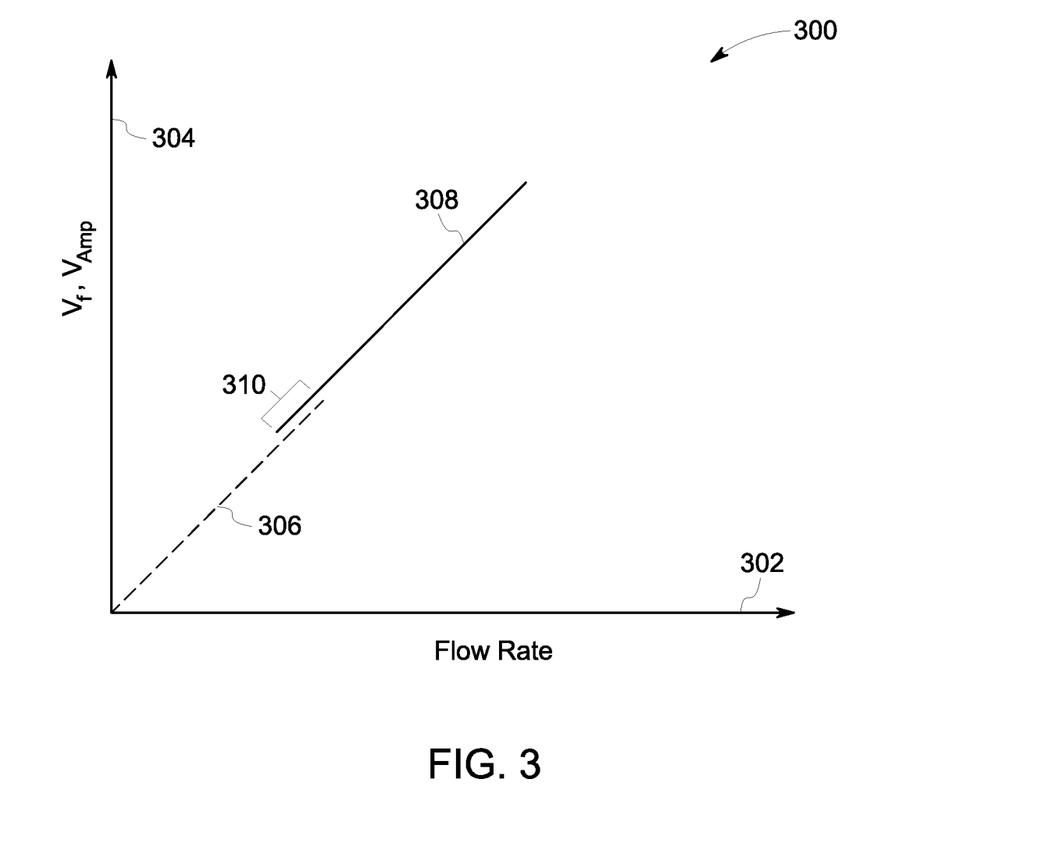
FIG. 3 is a graphical illustration depicting a response of a sensor in different flow regimes, in accordance with aspects of the present specification.

FIG. 3 is a graphical illustration 300 depicting a response of a sensor such as the flow sensor 210 of FIG. 2 in different flow regimes, in accordance with aspects of the present specification. FIG. 3 is explained in conjunction with the elements of FIG. 2. The X-axis 302 of the graphical illustration 300 represents a flow rate and the Y-axis 304 represents a magnitude ($V_{amp}$) and a frequency ($V_f$) of a voltage signal generated by the sensing element 211 of the flow sensor 210. The magnitude ($V_{amp}$) and the frequency ($V_f$) of the voltage signal generated by the flow sensor 210 may be referred to as a sensor response. As depicted in the graphical illustration 300, a first flow regime may be represented by a curve 306 and a second flow regime may be represented by a curve 308. It may be noted that in FIG. 3, the curves 306 and 308 are illustrated as straight lines for purposes of simplicity of illustration and should not be interpreted as an indication of a linear relationship between the flow rate 302 and the sensor response 304.

Also, reference numeral 310 is used to represent a flow regime, hereinafter referred to as a third flow regime, where the first flow regime 306 and the second flow regime 308 overlap. As depicted in FIG. 3, the third flow regime 310 is located near a lower end of the second flow regime 308. Therefore, in the third flow regime 310, vortices may be formed in the gas flowing in the flow conduit 222. Consequent to the formation of the vortices in the gas in the third flow regime 310, an AC voltage signal may be generated by the sensing element 211 of the flow sensor 210. However, the third flow regime 310 is also proximate to the first flow regime 306, thereby allowing measurement of an amplitude characteristic such as a magnitude ($V_{amp}$) of the voltage signal generated by the sensing element 211. Accordingly, the third flow regime 310 may be characterized by a range of flow rates in which both the temporal and amplitude characteristics of the voltage signal generated by the flow sensor 210 are measurable. In one embodiment, a parameter such as the magnitude ($V_{amp}$) of the voltage signal is used to represent amplitude characteristics of the voltage signal for the purpose of simplicity of the description. However, embodiments of the present specification are also applicable to other amplitude characteristics listed hereinabove.

Referring again to FIG. 2, characteristics of the third flow regime 310 (see FIG. 3) may be utilized to develop a calibration function. In one embodiment, the calibration function may be developed during a learning phase of the system 200. In another embodiment, the calibration function may be developed when the system 200 is operating to meter the gas. In yet another embodiment, the calibration function that is developed during the learning phase may be updated (continuously or at regular intervals of time) when the system 200 is operating to meter the gas. This dynamic updating of the calibration function when the system 200 is in operation may be referred to as an automatic recalibration of the system 200.

As will be appreciated due to the presence of the vortices in the second flow regime allows measurement of a volumetric flow rate of the gas in the housing 202. However, in the first flow regime, it may not be feasible to determine the volumetric flow rate due to the absence of vortices in the gas. In accordance with one aspect of the present specification, the system 200 may be configured to determine the calibration function to allow the system 200 to obtain the volumetric flow rate in the first flow regime. The calibration function represents a relationship between the volumetric flow rate determined based on the frequency ($V_f$) of the voltage signal and the mass flow rate determined based on the magnitude ($V_{amp}$) of the voltage signal in the third flow regime.

In one embodiment, during the learning phase, the system 200 may be configured to determine both the volumetric flow rate of the gas and the mass flow rate the gas for different flow rates in the third flow regime. For example, in the learning phase, the gas having a flow rate corresponding to the third flow regime is passed through the housing 202. The processor 212 may be configured to determine both the volumetric flow rate and the mass flow rate based on the frequency ($V_f$) and the magnitude ($V_{amp}$), respectively, of the voltage signal generated by the sensing element 211. In one embodiment, during the learning phase, the processor 212 may also be configured to obtain the values of the non-flow rate characteristics of the gas from the gas analyzer 207 while determining the volumetric flow rate and the mass flow rate. As previously noted, some examples of the non-flow rate characteristics of the gas may include one or more of the constituents of the gas, temperature, pressure, and caloric value of the gas, and/or levels of various impurities contained in the gas. This process may be repeated for different values of the flow rates corresponding to the third flow regime. The processor 212 may be configured to develop a calibration function based on the values of the volumetric flow rates, the mass flow rates, and one or more of the non-flow rate characteristics of the gas that correspond to the different flow rates associated with the third flow regime.

Once the calibration function is determined by the system 200 during the learning phase, the system 200 may be operatively coupled to the pipeline 214. As will be appreciated, vortices may or may not be formed in the fluid conduit 222 depending on the flow rate of the gas in the pipeline 214. In one embodiment, if the flow rate of the gas allows the formation of vortices in the gas (e.g., in the second flow regime), the AC voltage signal is generated by the sensing element 211. The processor 212 may be configured to determine a flow parameter such as the volumetric flow rate of the gas based on the frequency ($V_f$) of the AC voltage signal generated by the sensing element 211. In one embodiment, the processor 212 may utilize spectral analysis to determine the volumetric flow rate of the gas from the voltage signal. Moreover, in one embodiment, the processor 212 may also be configured to display the determined volumetric flow rate of the gas on the display 216.

In another embodiment, if the flow rate of the gas does not entail formation of the vortices in the fluid conduit 222 (e.g., in the first flow regime), the DC voltage signal may be generated by the sensing element 211. Accordingly, the processor 212 may determine the magnitude ($V_{amp}$) of the DC voltage signal. In such an instance, the processor 212 may be configured to determine the mass flow rate of the gas based on the magnitude ($V_{amp}$) of the voltage signal. Further, the processor 212 may be configured to determine the volumetric flow rate of the gas based on the calibration function that was developed during the learning phase of the system 200. Moreover, in one embodiment, the processor 212 may also be configured to display the determined volumetric flow rate of the gas on the display 216.

Additionally, the system 200 may also include the condition detector 218. In one embodiment, the condition detector 218 may be disposed on or about the housing 202. The condition detector 218 may be configured to detect occurrence of one or more environmental conditions and/or gas leakage from the system 200. The one or more environmental conditions include, but are not limited to, an earthquake, fire, flood, snow storm, storm, or combinations thereof. In order to detect the environmental conditions and/or the gas leakage, the condition detector 218 may include one or more sensors that aid in the detection of the earthquake, fire, flood, snow storm, gas leakage, storm, or combinations thereof. Moreover, the tampering detector 220 may also be disposed on or about the housing 202 and configured to detect any tampering of the system 200.

In one embodiment, the condition detector 218 may be configured to communicate signals indicative of the detection of the environmental conditions and/or the gas leakage to the processor 212. Also, in one embodiment, the tampering detector 220 may be configured to communicate signals indicative of the tampering of the system 200 to the processor 212. Upon receipt of the one or more such signals from the condition detector 218 and/or the tampering detector 220, the processor 212 may be configured to operate the shut-off valve to stop the flow of the gas through the housing 202.

In the presently contemplated configuration depicted in FIG. 2, the flow conduit 222 is shown as being disposed within the flow sensor 210. However, in some embodiments, the flow conduit 222 may be in fluid communication between the input port 204 and the output port 206 inside the housing 202. Moreover, in certain embodiments, the gas analyzer 207, the flow manager 208, and/or the flow disrupter 209 may be disposed in the flow conduit 222. In such a configuration, the flow sensor 210 may include the sensing element 211 disposed in the by-pass channel 224.

As previously noted, in the first flow regime, no vortices are formed in the gas flowing in the housing 202 and the sensing element 211 of the flow sensor 210 may generate the DC voltage having the amplitude characteristics such as the magnitude ($V_{amp}$). Also, in the second flow regime, the vortices are formed in the gas flowing in the housing 202 and the sensing element 211 may generate the AC voltage signal having the temporal characteristics such as the frequency ($V_f$). In accordance with aspects of the present specification, the system 200 may be configured to perform self-diagnosis in case of malfunctioning of one or more components of the system 200. In one embodiment, the processor 212 may be employed to aid in the self-diagnosis of the system 200. In one embodiment, the processor 212 may be employed to identify the one or more malfunctioning components. By way of example, the processor 212 may be configured to diagnose that the flow sensor 210 is malfunctioning if the amplitude characteristics of the DC voltage are significantly measurable in the second flow regime and/or the temporal characteristics of the AC voltage signal are significantly measurable in the first flow regime. One possible reason for such a malfunctioning of the flow sensor 210 may be an accumulation of impurities on or around the sensing element 211. In accordance with aspects of the present specification, once the malfunctioning of the flow sensor 210 is identified, the processor 212 may be configured to update the calibration function, thereby recalibrating the system 200. Recalibrating the system 200 aids in compensating for the effect of the accumulation of impurities on or around the sensing element 211.

Implementing the system 200 for metering gas as described with respect to FIG. 1 aids in determining flow parameters such as the mass flow rate of the gas, the accumulated volume of the gas, the volumetric flow rate of the gas, the cumulative gas volume per the determined time unit, or combinations thereof. More particularly, flow parameters may be determined corresponding to different flow regimes. Moreover, the flow parameters thus determined may not be impacted by gas density fluctuations, moisture fluctuations, gas mixture fluctuations, and the like.

Figure 4A:
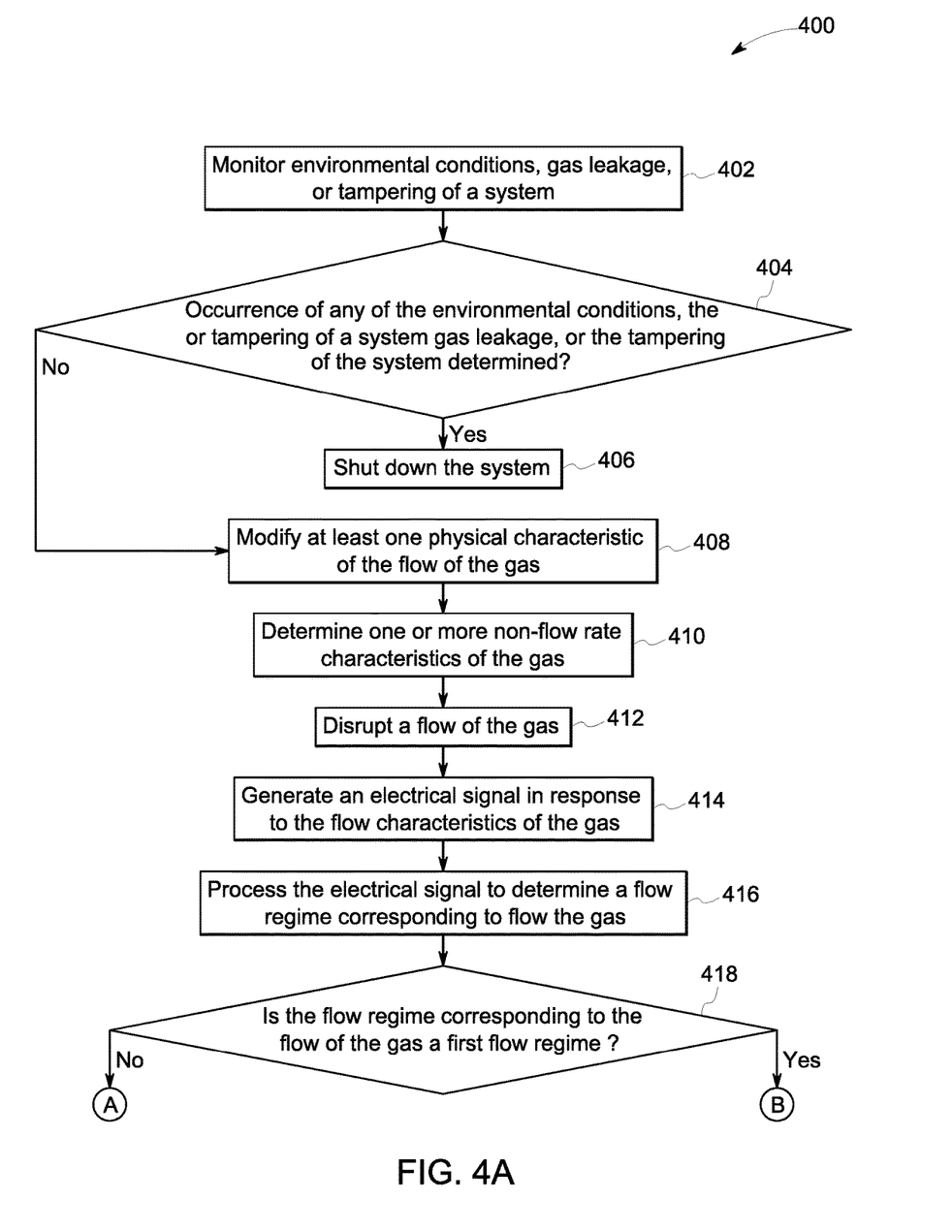
FIGS. 4A and 4B depict a flow chart illustrating an example method for metering gas, in accordance with aspects of the present specification.
Figure 4B:
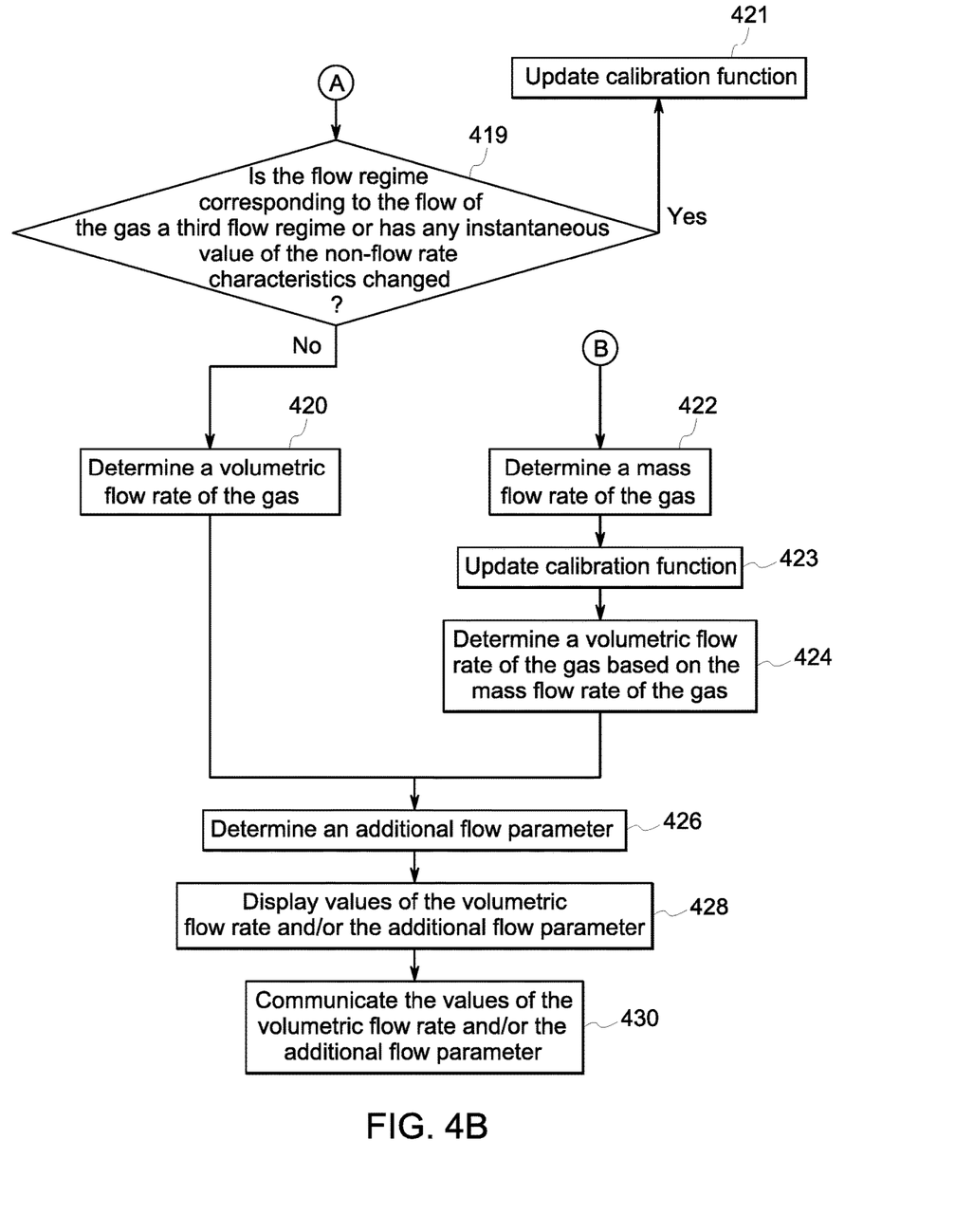

FIGS. 4A and 4B depict a flow chart 400 representative of an example method for metering gas, in accordance with aspects of the present specification. The method of FIGS. 4A and 4B is described in conjunction with the elements of FIG. 2. As noted previously, the system 200 includes the housing 202, the input port 204, the output port 206, the gas analyzer 207, the flow manager 208, and the flow sensor 210. The flow sensor 210 may include one or more of the flow conduit 222, the bypass channel 224, the flow disrupter 209, and the sensing element 211. The system 200 may further include the processor 212, display 216, condition detector 218, and tampering detector 220 disposed on or around the housing 202. In one example embodiment, the system 200 may be operatively coupled to the pipeline 214 and configured for metering the gas flowing through the pipeline 214.

In one embodiment, during a learning phase, the system 200 may be trained to develop a calibration function indicative of a relationship between a volumetric flow rate and a mass flow rate of the gas in a third flow regime. As previously noted, the third flow regime includes an overlap region of a first flow regime and a second flow regime. In another embodiment, the calibration function may be developed when the system 200 is operating to meter the gas. In yet another embodiment, the calibration function that is developed during the learning phase may be updated continuously or at regular intervals of time when the system 200 is operating to meter the gas.

Once the gas enters the system 200 through the input port 204, a portion of the gas may pass through the flow sensor 210. The gas from the housing 202 may exit from the output port 206.

As indicated by step 402, the system 200 may be configured to monitor one or more environmental conditions, gas leakage from the system 200 and/or tampering of the system 200. Some examples of the environmental conditions may include but, are not limited to, an earthquake, fire, flood, snow storm, storm, or combinations thereof. As noted previously, the one or more environmental conditions and/or the gas leakage may be monitored by the condition detector 218. The tampering of the system 200 may be monitored by the tampering detector 220.

Further, a check may be carried out at step 404 to determine occurrence of one or more of the environmental conditions, gas leakage from the system 200, and/or tampering of the system 200. In one embodiment, the condition detector 218 and/or the tampering detector 220 are configured to generate signals indicative of the occurrence of environmental conditions, gas leakage from the system 200, and/or tampering of the system 200. The processor 212 is configured to detect the occurrence of any of the environmental conditions, gas leakage from the system 200, and/or tampering of the system 200 based on the signals received from the condition detector 218 and/or the tampering detector 220. At step 404, if the occurrence of any of the environmental conditions, the gas leakage, or the tampering is determined, the system 200 may be shut down, as indicated by step 406. In another embodiment, the system 200 may be shut down in case of certain billing related issues. For example, the system 200 may be shut down if a customer fails to pay a bill within a prescribed duration. In order to shut down the system 200, in one embodiment, the processor 212 is configured to operate a shut-off valve located within the flow manager 208 to stop the flow of the gas through the flow conduit 222.

Although, the flow chart 400 of FIGS. 4A-4B depicts steps 402, 404, and 406 as being performed at the outset, it may be noted that steps 402-406 may be performed at any time during the process of metering the gas. In one embodiment, the environmental conditions, gas leakage, and tampering of the system 200 may be continuously monitored while the system 200 is in operation.

However, at step 404, if it is determined that the environmental conditions or the gas leakage did not occur and/or the system 200 has not been tampered with, at least one physical characteristic of the flow of the gas in the flow conduit 222 may be modified, as indicated by step 408. As will be appreciated, physical characteristics including, but not limited to, a separability of the flow of the gas, pressure of the gas, temperature of the gas, level of impurities in the gas, or combinations thereof may affect measurement results. Accordingly, it may be desirable to account for one or more of these physical characteristics while metering of the gas. Consequently, at least one physical characteristic of the flow of the gas is modified, as indicated by step 408. In one example, the at least one physical characteristic may be modified by the flow manager 208 under the control of the processor 212.

Subsequently, at step 410, one or more non-flow rate characteristics of the gas may be determined. In one embodiment, the one or more non-flow rate characteristics may be determined by the gas analyzer 207. Some examples of the non-flow rate characteristics may include but, are not limited to, a gas density, gas temperature, gas pressure, gas mixture, energy content of the gas, levels of various impurities contained in the gas, or combinations thereof. In one embodiment, when a flow disrupter such as the flow disrupter 209 is disposed within the gas analyzer 207, the flow disrupter 209 may also aid in the determination of non-flow rate characteristics.

In addition, at step 412, the flow of the gas in the housing 202 and/or flow conduit 222 may be disrupted by the flow disrupter 209. In one embodiment, at least some flow characteristics of the gas may be modified due to disturbances imparted by the flow disrupter 209 in the flow of the gas. For example, depending on the flow rate of the gas, vortices may be formed in the gas flowing in the flow conduit 222.

Also, an electrical signal may be generated by the flow sensor 210 in response to the flow characteristics of the gas in the housing 202, as indicated by step 414. In one embodiment, the sensing element 211 may be employed in the flow sensor 210 to generate the electrical signal. As noted previously, if no vortices are formed in the gas, a DC voltage signal may be generated by the sensing element 211. However, if the vortices are formed in the gas, an AC voltage signal may be generated by the sensing element 211. In certain embodiments, the AC voltage signal may also have a DC value. Amplitude characteristics and/or temporal characteristics of the voltage signal may be proportional or directly related to the flow rate of the gas flowing through the flow conduit 222. The electrical signal (e.g., the voltage signal) generated by the sensing element 211 may then be processed to determine a flow regime corresponding to the flow of the gas, as indicated by step 416. In one embodiment, the voltage signal may be processed by the processor 212 by performing spectral analysis of the electrical signal to determine the flow regime.

Accordingly, at step 418, a check may be carried out to determine whether the flow regime corresponding to the flow of the gas flowing through the system 200 is the first flow regime. In one embodiment, the processor 212 may be used to determine the flow regime corresponding to the flow of the gas flowing through the system 200.

In one embodiment, if a DC signal is received by the processor 212 from the flow sensor 210, the processor 212 may be configured to determine that the flow regime of the flow rate of the gas is the first flow regime. By way of example, if the frequency of the voltage signal received from the flow sensor 210 has a value of zero, the processor 212 may be configured to determine that the flow regime of the flow rate of the gas is the first flow regime. In another example, the processor 212 may be configured to determine that the flow regime of the flow rate of the gas is the first flow regime based on a DC voltage level of the voltage signal.

At step 418, if it is determined that the flow regime corresponding to the flow of the gas is the first flow regime, a mass flow rate may be determined based on the amplitude characteristics of the DC voltage signal, as indicated by step 422. In one embodiment, the mass flow rate of the gas is determined by the processor 212.

Moreover, at step 423, the calibration function is updated. The calibration function may be updated depending on the instantaneous values of the non-flow rate characteristics such as one or more of the constituents of the gas, temperature, pressure, and caloric value of the gas, and/or levels of various impurities contained in the gas. In one embodiment, for a first time use of the system 200, updating of the calibration function includes developing the calibration function.

Thereafter, at step 424, the volumetric flow rate of the gas may be determined by the processor 212 based on the mass flow rate of the gas determined at step 422. In another embodiment, the processor 212 may be configured to determine the volumetric flow rate of the gas by processing mass flow rate of the gas via the use of the calibration function determined during the learning phase or the updated calibration function determined at step 423. Control may be passed to step 426.

With returning reference to step 418, if an AC voltage signal is received by the processor 212 from the flow sensor 210, the processor 212 may be configured to determine that the flow regime corresponding to the flow of the gas is not the first flow regime. By way of example, if the frequency of the voltage signal has a non-zero value, the processor 212 may be configured to determine that the flow regime corresponding to the flow rate of the gas is not the first flow regime.

At step 418, if it is determined that the flow regime corresponding to the flow of the gas is not the first flow regime, an additional check may be carried out at step 419 to determine if the flow regime corresponding to the flow of the gas is the third flow regime or any instantaneous value of the non-flow rate characteristics has been changed. If it is determined that the flow regime corresponding to the flow of the gas is the third flow regime or any instantaneous value of the non-flow rate characteristics has been changed, the calibration function determined during the learning phase may be updated as indicated by step 421. The calibration function may be updated depending on the instantaneous values of the non-flow rate characteristics such as one or more of the constituents of the gas, temperature, pressure, and caloric value of the gas, and/or levels of various impurities contained in the gas. In one embodiment, for a first time use of the system 200, updating of the calibration function may include developing the calibration function.

However, at step 419, if it is determined that neither the flow regime corresponding to the flow of the gas is the third flow regime nor there has been any change in the instantaneous value of the non-flow rate characteristics, the processor 212 may be configured to determine that the flow regime corresponding to the flow rate of the gas is the second flow regime. Consequently, a volumetric flow rate of the gas may be determined based on the temporal characteristics of the AC voltage signal, as depicted by step 420. In one embodiment, the volumetric flow rate of the gas is determined by the processor 212. Control may be passed to step 426.

At step 426, an additional flow parameter may be determined. In one embodiment, the additional flow parameter such as an accumulated volume of the gas may be determined by the processor 212 based on the volumetric flow rate determined at either at step 420 or step 424. As noted previously, the calibration function has been developed and/or updated depending on the instantaneous values of the temperature and/or pressure of the gas in the housing 202. Consequently, as the volumetric flow rate and/or the additional flow parameter are determined after processing the mass flow rate of the gas via the updated calibration function, the determined values of the volumetric flow rate and/or the additional flow parameter may be representative of temperature and/or the pressure corrected values of the volumetric flow rate and/or the additional flow parameter.

Moreover, the determined values of volumetric flow rate and/or the additional flow parameter may be visualized on displays as indicated at step 428. In one embodiment, the processor 212 is configured to display the volumetric flow rate and/or the additional flow parameter on the display 216.

Additionally, in certain embodiments, the values of the volumetric flow rate and/or the additional flow parameter may be communicated to a remote location as indicated by step 430. In some embodiments, the values of the volumetric flow rate and/or the additional flow parameter may be communicated to one or more displays disposed at a remote location. In one embodiment, the processor 212 may be configured to communicate the values of the volumetric flow rate and/or the additional flow parameter to the one or more remotely located displays over a wireless communication.

In certain embodiments, the determined values of the volumetric flow rate and the additional flow parameters such as the accumulated volume of the gas may be used to bill respective customer. More particularly, a bill amount may be determined based on the accumulated volume of the gas.

Any of the foregoing steps and/or system elements may be suitably replaced, reordered, or removed, and additional steps and/or system elements may be inserted, depending on the needs of a particular application, and that the systems of the foregoing embodiments may be implemented using a wide variety of suitable processes and system elements and are not limited to any particular computer hardware, software, middleware, firmware, microcode, etc.

The system and method for metering gas described hereinabove greatly improves the accuracy of measurement of the flow parameters of the gas such as the volumetric flow rate of the gas. Use of the non-flow rate characteristics of the gas in developing the calibration function aids in enhancing the accuracy of the measurement of the flow parameters. Moreover, the flow manager aids in maintaining one or more physical characteristics of the flow of the gas within corresponding desired limits thereby minimizing the effect of the physical characteristics on the accuracy of the measurement of the flow parameters. Also, the system facilitates a hazard free setup as the system is configured to stop the flow of the gas on detection of occurrence of an earthquake, fire, flood, snow, gas leakage, tsunami, or tampering of the system. Additionally, use of electronic sensing elements leads to increased mass production and reduces overall cost of manufacturing of such gas metering systems.

Furthermore, the system is also capable of performing self-diagnosis in case of malfunctioning of one or more components of the system. Also, the automated recalibration of the system aids in mitigating the influence of the impurities in the gas on the measurements performed by the system. Consequently, the accuracy of the measurements may be maintained for the lifetime and operation of the system. In addition, the measurement of the volumetric flow rate based on the vortices is impervious to any impurities in the gas.

The foregoing examples, demonstrations, and method steps such as those that may be performed by the system may be implemented by suitable code on a processor-based system, such as a general-purpose or special-purpose computer. Different implementations of the systems and methods may perform some or all of the steps described herein in different orders, parallel, or substantially concurrently. Furthermore, the functions may be implemented in a variety of programming languages, including but not limited to C++ or Java. Such code may be stored or adapted for storage on one or more tangible, computer readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

It will be appreciated that variants of the above disclosed and other features and functions, or alternatives thereof, may be combined to create many other different systems or applications. Various unanticipated alternatives, modifications, variations, or improvements therein may be subsequently made by those skilled in the art and are also intended to be encompassed by the following claims.

The invention claimed is:

1. A system for metering gas, comprising:
   a housing comprising an input port and an output port, wherein the housing is configured to allow a flow of the gas between the input port and the output port;
   a flow manager disposed in the housing and configured to modify at least one physical characteristic of the flow of the gas in the housing;
   a flow sensor disposed in the housing and configured to generate an electrical signal in response to a flow characteristic of the gas in the housing; and
   a processor operatively coupled to the flow manager and the flow sensor and configured to identify a flow regime for the gas and to determine a flow parameter of the gas that corresponds with the flow regime,
   wherein in a first flow regime, the flow parameter of the gas corresponds with an amplitude characteristic of the electrical signal, in a second flow regime, the flow parameter corresponds with a temporal characteristic of the electrical signal, and in a third flow regime, the flow parameter of gas corresponds with a calibration function that uses both the amplitude characteristic and the temporal characteristic of the electrical signal across a region of overlap between the amplitude characteristic and the temporal characteristic.

2. The system of claim 1, wherein the flow sensor comprises one or more first sensing elements, and wherein the one or more first sensing elements comprise micro-electromechanical flow sensing elements, thermopiles, temperature flow sensor sensing elements, pressure sensing elements, or combinations thereof.

3. The system of claim 2, wherein the flow sensor comprises at least one of a first flow conduit and a first bypass channel.

4. The system of claim 1, wherein the flow parameter comprises a mass flow rate of the gas, an accumulated volume of the gas, a volumetric flow rate of the gas, a cumulative gas volume per a determined time unit, or combinations thereof.

5. The system of claim 1, wherein the first flow regime comprises a range of flow rates of the gas in the housing that impedes application of disturbances to the flow of the gas.

6. The system of claim 1, wherein the second flow regime comprises a range of flow rates of the gas in the housing that allows disturbances to be imparted to the flow of the gas.

7. The system of claim 1, wherein, in the first flow regime, the calibration function is indicative of a relationship at least between a volumetric flow rate of the gas and a mass flow rate of the gas.

8. The system of claim 1, further comprising a gas analyzer disposed in the housing and configured to determine one or more non-flow rate characteristics of the gas, wherein the one or more non-flow rate characteristics of the gas comprise a gas density, a gas temperature, a gas pressure, a gas mixture, an energy content of the gas, or combinations thereof.

9. The system of claim 1, wherein the housing further comprises one or more second sensing elements disposed in the second bypass channel, and wherein the one or more second sensing elements comprise micro-electromechanical flow sensing elements, thermopiles, temperature flow sensor sensing elements, pressure sensing elements, or combinations thereof.

10. A method for metering gas, comprising:
    modifying at least one physical characteristic of a flow of the gas in a housing;
    generating an electrical signal in response to a flow characteristic of the gas in the housing;
    identifying a flow regime of the gas, the flow regime based on characteristics of the electrical signal, wherein a first flow regime corresponds with an amplitude characteristic of the electrical signal, a second flow regime corresponds with a temporal characteristic of the electrical signal, and a third flow regime corresponds with overlap between both the amplitude characteristic and the temporal characteristic of the electrical signal; and
    determining a flow parameter that corresponds with the flow regime,
    wherein the flow parameter in the third flow regime corresponds with a calibration function that uses both the amplitude characteristic and the temporal characteristic of the electrical signal across a region of overlap between the amplitude characteristic and the temporal characteristic.

11. The method of claim 10, further comprising determining non-flow rate characteristics of the gas, a tampering of a system, a gas leakage from the system, and one or more environmental conditions.

12. The method of claim 10, further comprising determining, in the first flow regime, the flow parameter based at least on the calibration function.

* * * * *